United States Patent
Buckley et al.

(10) Patent No.: US 9,314,352 B1
(45) Date of Patent: Apr. 19, 2016

(54) ENDOPROSTHESIS HAVING OPEN FLOW LUMENS

(71) Applicant: W. L. Gore & Associates, Inc., Newark, DE (US)

(72) Inventors: Kyle R. Buckley, Flagstaff, AZ (US); Benjamin I. Espen, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 50 days.

(21) Appl. No.: 13/858,549

(22) Filed: Apr. 8, 2013

Related U.S. Application Data

(60) Provisional application No. 61/625,603, filed on Apr. 17, 2012.

(51) Int. Cl.
*A61F 2/06* (2013.01)
*A61F 2/82* (2013.01)

(52) U.S. Cl.
CPC ............ *A61F 2/82* (2013.01); *A61F 2002/828* (2013.01); *A61F 2220/0091* (2013.01)

(58) Field of Classification Search
CPC ... A61F 2/07; A61F 2002/07; A61F 2002/65; A61F 2/82; A61F 2220/0091; A61F 2220/828
USPC ........... 623/1.11, 1.12, 1.14, 1.35, 1.36, 1.16, 623/1.15
See application file for complete search history.

(56) References Cited

U.S. PATENT DOCUMENTS

| | | | |
|---|---|---|---|
| 5,693,088 A * | 12/1997 | Lazarus | 623/1.35 |
| 6,475,237 B2 * | 11/2002 | Drasler et al. | 623/1.15 |
| 6,673,107 B1 * | 1/2004 | Brandt et al. | 623/1.35 |
| 9,005,274 B2 * | 4/2015 | Seguin et al. | 623/1.35 |
| 2002/0120327 A1 * | 8/2002 | Cox et al. | 623/1.16 |
| 2004/0172127 A1 * | 9/2004 | Kantor | 623/1.16 |
| 2007/0005127 A1 * | 1/2007 | Boekstegers | A61F 2/2493 623/1.16 |
| 2010/0331958 A1 * | 12/2010 | Chobotov | A61F 2/07 623/1.15 |

* cited by examiner

*Primary Examiner* — Todd E Manahan
*Assistant Examiner* — Majid Jamialahmadi

(57) ABSTRACT

Exemplary embodiments of the present invention comprise a stent graft having a first section and a second section, wherein the first section comprises a first longitudinal profile and a first flow lumen and the second section comprises a second longitudinal profile and a second flow lumen. In exemplary embodiments, a hinged connection between the first and second sections is structurally and/or materially configured to isolate or otherwise not transfer bending forces between the first and second sections.

18 Claims, 5 Drawing Sheets

ENDOPROSTHESIS HAVING OPEN FLOW LUMENS

CROSS REFERENCE TO RELATED APPLICATIONS

This application claims priority to U.S. Provisional Application No. 61/625,603, filed Aug. 17, 2012. The disclosure of the prior application is considered part of and is incorporated by reference in the disclosure of this application.

BACKGROUND OF THE INVENTION

1. Field of the Invention

The present invention relates to improved endoprostheses for treating disease of the vasculature.

2. Discussion of the Related Art

Endoprostheses are commonly used for treating disease of the vasculature. By way of example, bifurcated stent grafts may be used in the treatment of abdominal aortic aneurisms, which generally affect the abdominal aorta and may extend down into the iliac arteries. More generally, stents and stent grafts may be used in various indications to reinforce the vasculature and/or otherwise provide an open flow lumen.

Due to the tortuous nature of the vasculature, not only does navigating an endoprosthesis to a treatment site present considerable difficulties, but providing a continuous open flow lumen post deployment through twists and turns in the tortuous vasculature has heretofore been a challenge. In particular, existing stent grafts have a tendency to kink when bent to accommodate a treatment site having a twist or turn, thus closing their lumens to open flow.

Returning to the earlier example, in the treatment of abdominal aortic aneurisms a bifurcated stent graft is often anchored in the abdominal aorta just inferior to the renal arteries and extends down to a bifurcation region and into the iliac arteries. Between the anchors and the bifurcation region, the abdominal aorta may turn up to ninety degrees or more. Existing stent grafts may exhibit kinks at this turn, partially or completely obstructing flow therethrough.

There is thus a need in the art for endoprostheses configured to be deployed around twists and turns in the tortuous vasculature and still maintain open flow lumens.

SUMMARY OF THE INVENTION

Exemplary embodiments of the present invention comprise an endoprosthesis having a first section and a second section. The first section comprises a first longitudinal profile and a first flow lumen. The second section comprises a second longitudinal profile and a second flow lumen and, optionally in the embodiment of a bifurcated endoprosthesis, a third longitudinal profile and a third flow lumen wherein the second and third lumens have smaller diameters than the first lumen. In exemplary embodiments, the endoprosthesis comprises a support component and a graft component. The support component is preferably nitinol and the graft component is preferably wrapped ePTFE.

In exemplary embodiments, the longitudinal profiles are not collinear, not parallel, or are otherwise bent relative to each other post deployment, yet the flow lumens remain substantially open and unkinked. In exemplary embodiments, a hinged connection between the first and second sections maintains the flow lumens substantially open and unkinked despite the endoprosthesis being bent. In general, the hinged connection is structurally and/or materially configured to isolate or otherwise not transfer bending forces between the first and second sections.

Methods for maintaining flow lumens of endoprostheses substantially open and unkinked are also disclosed.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 2A-3B illustrate side and end views of an exemplary bifurcated endoprosthesis in a straight configuration.

FIGS. 3A-3B illustrate side and end views of an exemplary bifurcated endoprosthesis in a bent configuration.

DETAILED DESCRIPTION OF THE ILLUSTRATED EMBODIMENTS

Figure 1A:
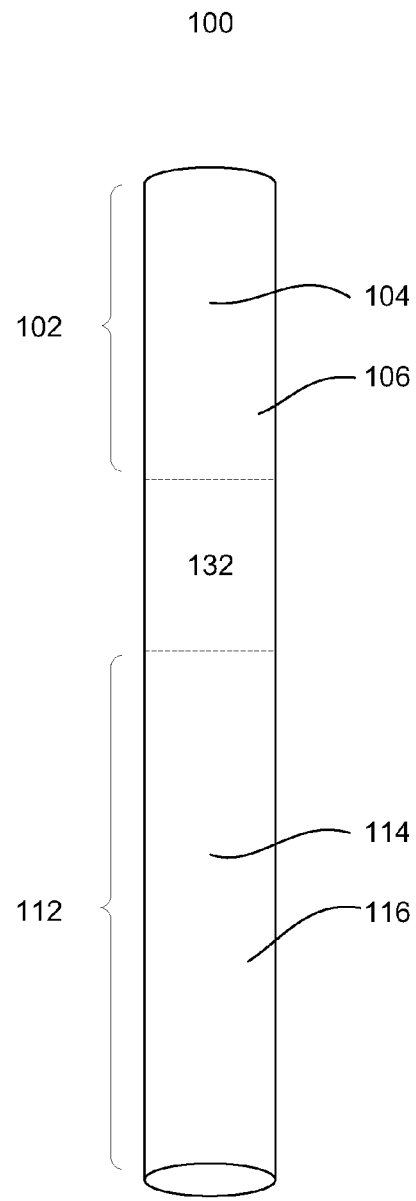
FIGS. 1A-1B illustrate an exemplary endoprosthesis in straight and bent configurations.

Persons skilled in the art will readily appreciate that various aspects of the present invention may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present invention, and in that regard, the drawing figures should not be construed as limiting. Finally, although the present invention may be described in connection with various principles and beliefs, the present invention should not be bound by theory.

In general, the present invention relates to endoprostheses configured to be deployed around twists and turns in the tortuous vasculature and still maintain open flow lumens.

In exemplary embodiments, the endoprosthesis comprises a support component and a graft component, such as in a stent graft. In preferred embodiments, the endoprosthesis may consist of a plurality of support components and a single, continuous graft component.

A graft component is generally any abluminal (i.e., outer, vessel surface) or luminal (i.e., inner, blood flow surface) covering configured to partially or substantially cover one or a plurality of support components.

In preferred embodiments, a graft component comprises wrapped ePTFE. However, other useful materials for the graft component may comprise one or more of nylons, polycarbonates, polyethylenes, polypropylenes, polytetrafluoroethylenes, polyvinyl chlorides, polyurethanes, polysiloxanes, and other biocompatible materials.

An exemplary graft component is fixedly secured or otherwise coupled at a single or a plurality of locations to the abluminal or luminal surface of the support component, for example, using one or more of taping, heat shrinking, adhesion and other processes known in the art. In some exemplary embodiments, a plurality of graft components are used and may be coupled to both the abluminal and luminal surfaces of the support component(s). In other exemplary embodiments, a plurality of graft components "sandwich" the support component(s), the graft components being attached to each other.

In exemplary embodiments, a support component has dimensions appropriate for the given treatment and may provide structural support for the graft component of the endoluminal device and/or the vasculature to be treated. A support component may be a stent comprised either of a wire having a helical configuration or be comprised of one or a plurality of rings. Among other configurations, the wire or a ring itself may be linear or have a sinusoidal or zig-zag pattern. Still another exemplary support component may be cut from a tube and have any pattern suitable for the treatment.

The support component is preferably comprised of a shape-memory material, such as nitinol. In other embodiments, however, the support component may be comprised of other materials, self-expandable or otherwise expandable (e.g., with a conventional balloon catheter or spring mechanism), such as various metals (e.g., stainless steel), alloys and polymers.

Exemplary embodiments of the present invention comprise an endoprosthesis having a first section and a second section. The first section generally comprises a first longitudinal profile and a first flow lumen. Similarly, the second section generally comprises a second longitudinal profile and a second flow lumen.

As used herein, "flow lumen" is a defined conduit or other passageway for liquid or other material that is partially or totally enclosed except for one or a plurality of open ends or side branch openings. As used herein, "longitudinal profile" is the curvature or other spatial variation of a flow lumen from one of its ends to the other, may vary along the length of a flow lumen, can be in the x, y and/or z direction, and, post deployment, may generally be said to correspond to the natural or anomalous pathway taken by the tortuous vasculature at and/or surrounding a treatment site.

Exemplary endoprostheses may be configured to conform to the pathway taken by the vasculature or may be biased to provide a reinforced and/or a corrected pathway.

Optionally, for example in the embodiment of a bifurcated endoprosthesis, the second section may comprise a third longitudinal profile and a third flow lumen. In this exemplary embodiment of a bifurcated endoprosthesis, the second and third lumens may have smaller diameters than the first lumen.

The cross-section of the various sections may be circular, ovoidal, or have polygonal features with or without curved features. The cross-sectional shape of the various sections may be either substantially constant or variable along its longitudinal profile. In like manner, the cross-sectional surface area of the various sections may be either substantially constant or variable along its longitudinal profile. In a preferred embodiment of a bifurcated endoprosthesis, the first section's cross-section is substantially circular at its distal end but tapers to have an ovoidal rectangular cross-section with a smaller cross-sectional surface area in its bifurcation region.

Figure 1B:
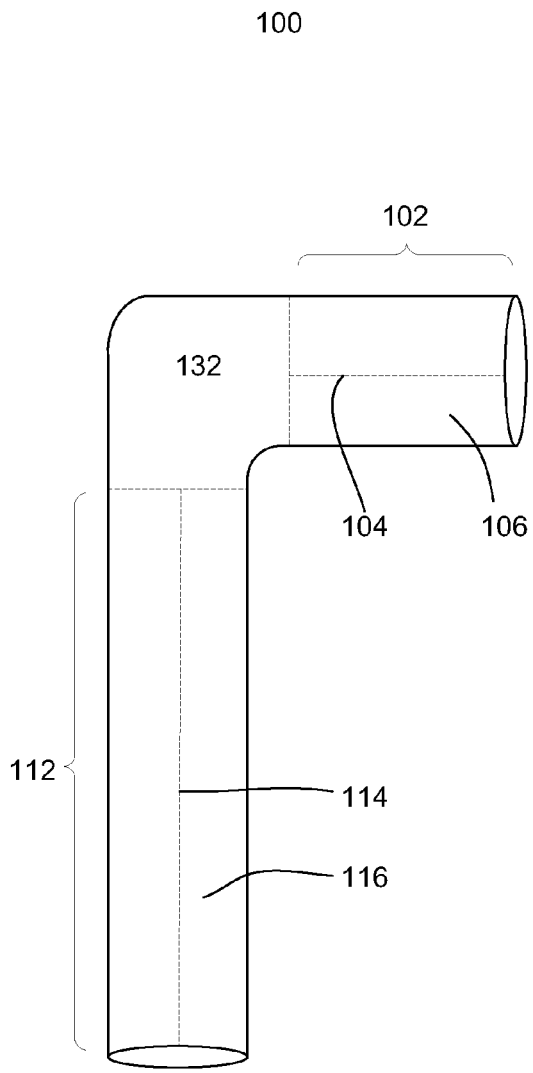

With reference now to FIGS. 1A-1B, exemplary endoprostheses 100 of the present invention comprise a first section 102 and a second section 112. The first section 102 may comprise a first longitudinal profile 104 and a first flow lumen 106, and the second section 112 may comprise a second longitudinal profile 114 and a second flow lumen 116.

In order to conform to the tortuous nature of the vasculature post deployment, the longitudinal profiles of the first and second sections of an exemplary endoprosthesis are not collinear, not parallel, or are otherwise bent or twisted relative to each other.

Nevertheless, in preferred embodiments, the flow lumens within the first and second sections remain substantially open and unkinked. As used herein, "open," "unkinked" are used interchangeably and generally mean not significantly closed, restricted or otherwise obstructed, whether partially or completely, but rather, free to allow passage of liquid or other material therethrough, whether along a straight path or about a twist or turn, and in some embodiments, defined by a smooth inner surface.

In exemplary embodiments, a hinged connection 132 between the first section 102 and the second section 112 maintains the flow lumens substantially open and unkinked despite the endoprosthesis being bent or twisted. Importantly, the hinged connection 132 may overlap and even be comprised of a portion of one or both of the first section 102 and the second section 112. In the alternative, and as illustrated in FIGS. 1A-1B, the hinged connection 132 may be separate and distinct from the first section 102 and the second section 112.

In general, the hinged connection is any structural and/or material configuration that isolates or otherwise does not transfer bending or twisting forces between the first and second sections.

An exemplary structural configuration comprises flow lumens exhibiting diameter differential. For instance, the first and second or third flow lumens may exhibit diameter differential. Alternatively, the diameter of the first flow lumen may be different from the combined diameter of the second and third flow lumens. In such embodiments, adjacent ends of the flow lumens have different diameters to allow one to move, at least partially, into the other at the hinged connection to allow for relative bending or twisting of the first and second sections. In exemplary embodiments, the relative movement into the other varies and is greatest on the inside of the bend or twist accommodated by the hinged connection. More generally, adjacent ends of the flow lumens may be structurally configured to telescope relative to one another at the hinged connection in any manner that provides for relative bending or twisting of the first and second sections.

Another exemplary structural configuration of the hinged connection comprises at least one or a plurality of pleats formed between the first and second sections when the endoprosthesis is bent or twisted. This may be accomplished, for example, by attaching support components to the graft component by a film that only partially covers the undulations of the support components, as described below.

The hinged connection may be materially the same or different as compared with the first and second sections. For instance, the hinged connection may be an integral, seamless extension of and existing between the first and second sections, comprising, for example, a support component and a plurality of graft components.

However, the hinged connection comprises neither a support component nor a graft component. Indeed, in exemplary embodiments, the hinged connection is free from any metallic element. By way of non-limiting example, in exemplary embodiments, the hinged connection may be comprised at least partially of a material exhibiting elastic properties to isolate or otherwise not transfer bending or twisting forces between the first and second sections.

Figure 2A:
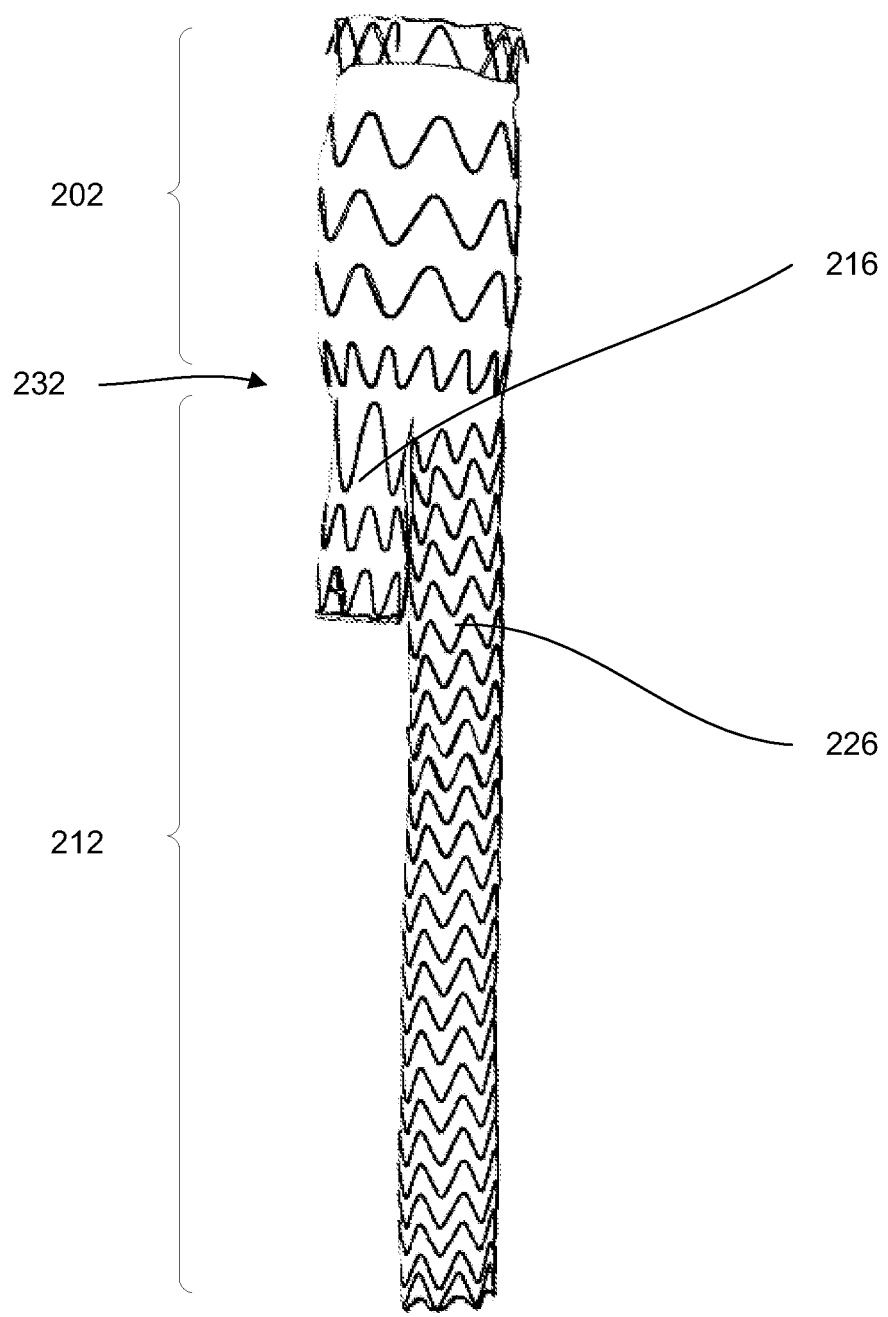
Figure 2B:
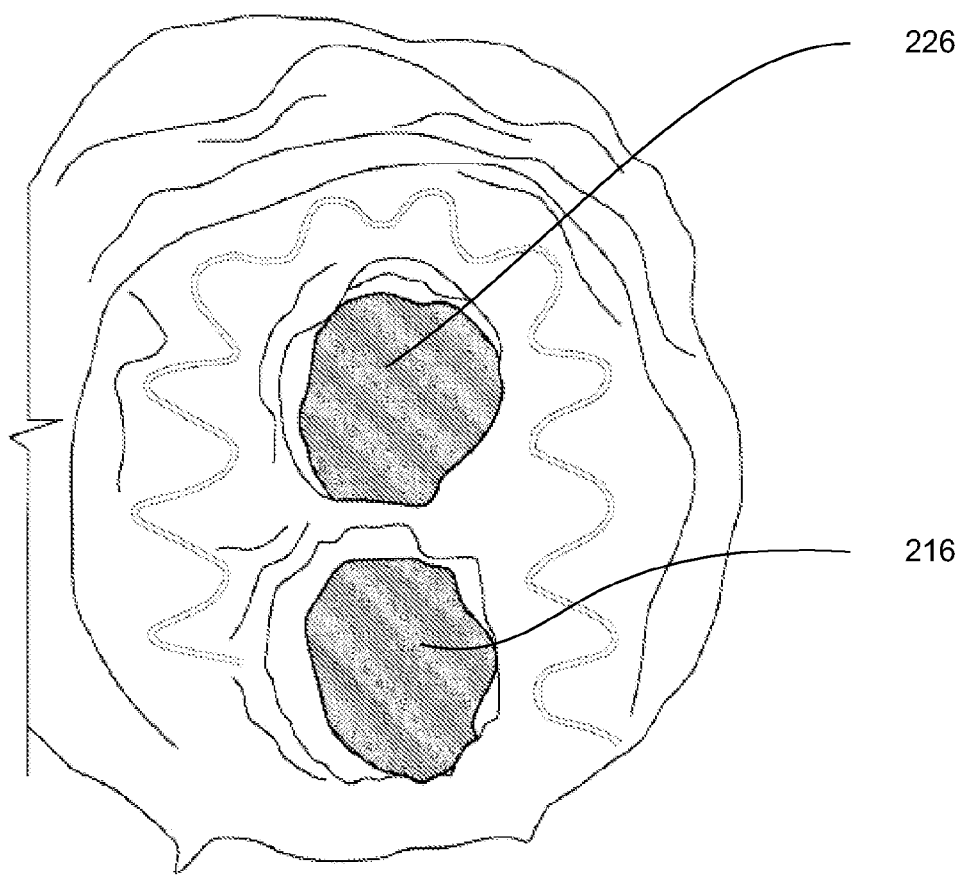

With reference now to the exemplary bifurcated endoprosthesis embodiment depicted in FIGS. 2A-2B, the first section 202 of the endoprosthesis has three individual ring support components, each formed from an undulating wire. The wire ring support components are attached to the graft component by a film that only partially covers the wire undulations. This configuration allow the first section 202 to bend at the hinged connection 232 within 360 degrees without kinking.

Below the three ring support components is a fourth ring support component formed from an undulating wire. The fourth support component is preformed with an outward circumferential bias, encouraging it to tilt and spring open, away from the endoprosthesis.

Two flow lumens 216 and 226 (i.e., the second section 212) are formed below to the biased ring support component, forming a bifurcation area. The two flow lumens 216 and 226 have individual support components located below the bifurcation. In this particular embodiments, there is no support component bridging the area between the biased support component, bifurcation and the two flow lumens 216 and 226.

Figure 3A:
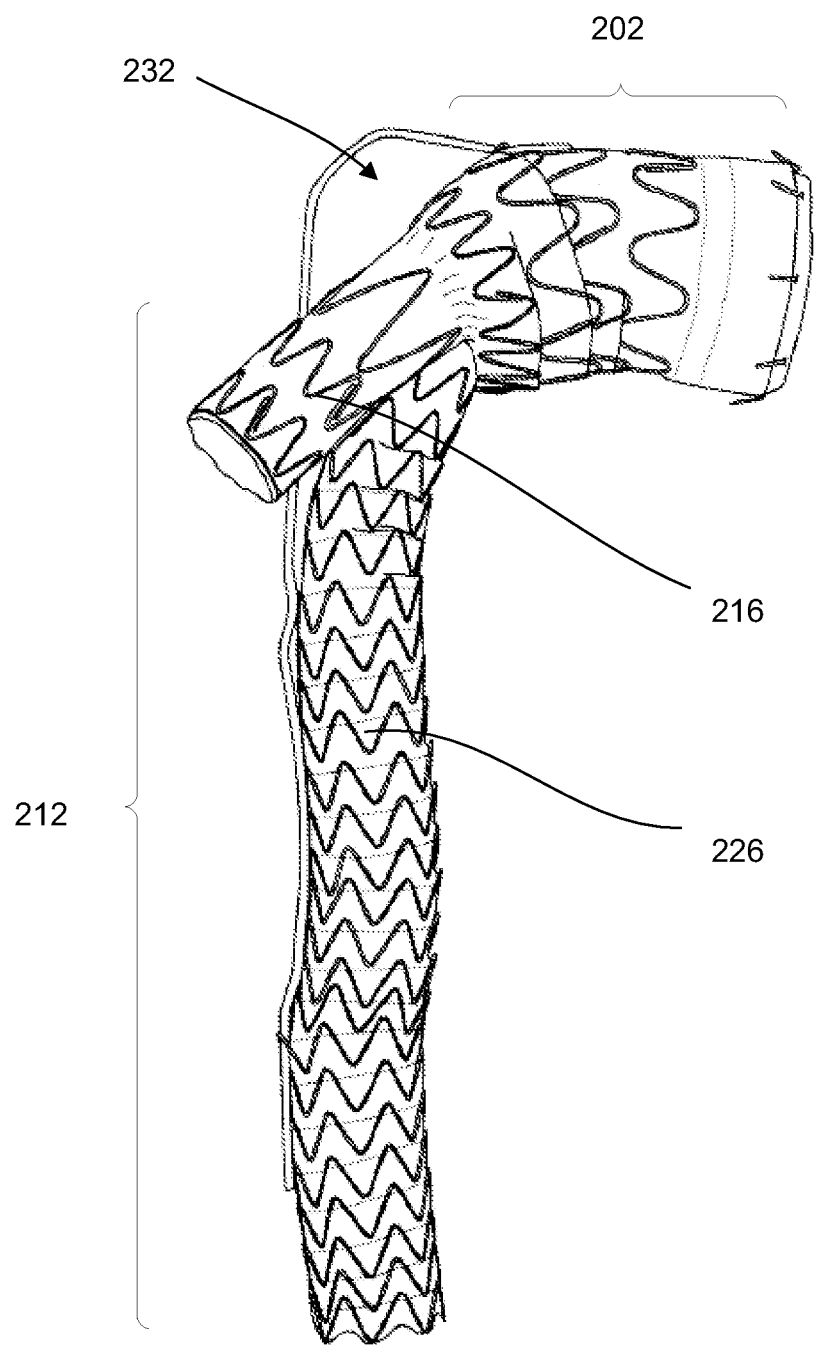
Figure 3B:
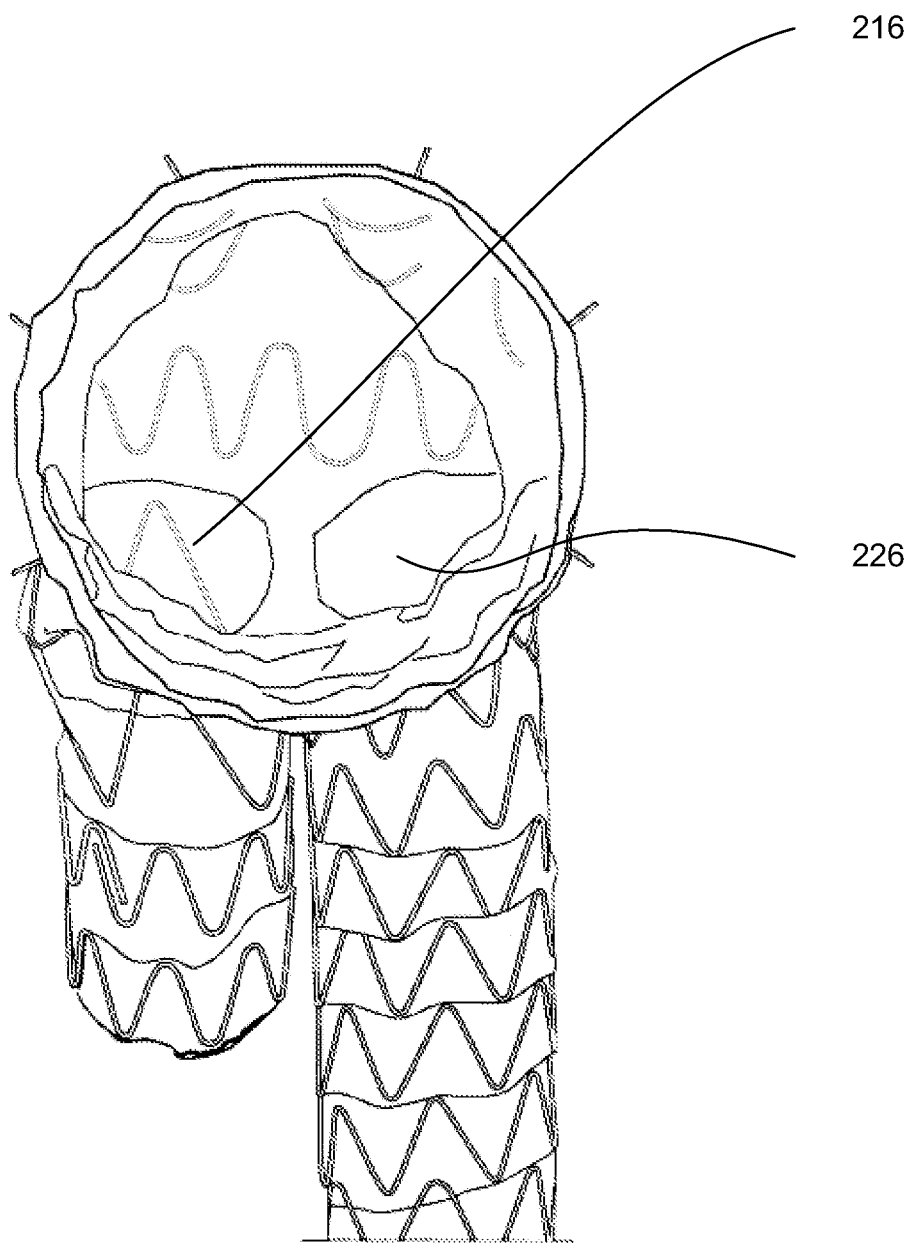

In sum, when the first section 202 is bent or twisted to conform to a vessel (as illustrated in FIGS. 3A-3B), the bending or twisting forces are isolated and not transmitted to the bifurcation or the two flow lumens 216 and 226. This lack of bending or twisting force transmission keeps the two flow lumens 216 and 226 fully open when the first section 202 is bent or twisted. Compare the openness of the two flow lumens 216 and 226 in FIG. 2B and FIG. 3B, the former illustrating the endoprosthesis in a straight configuration and the latter illustrating the endoprosthesis in a perpendicularly bent configuration.

The present invention also encompasses methods for maintaining flow lumens of endoprostheses substantially open and unkinked. An exemplary method for maintaining flow lumens of an endoprosthesis substantially open and unkinked comprises deploying an endoprosthesis as described above at a treatment site, wherein the treatment site comprises one of a twist and turn.

It will be apparent to those skilled in the art that various modifications and variations can be made in the present invention without departing from the spirit or scope of the invention. For instance, while the present invention has been described primarily with reference to a single hinged connection, use of a plurality of hinged connections is contemplated. Thus, it is intended that the present invention cover the modifications and variations of this invention provided they come within the scope of the appended claims and their equivalents.

What is claimed is:

1. An endoprosthesis comprising:
   a single, continuous graft component having an uninterrupted outer surface combined with a plurality of support components, the combination comprising:
   a first section having a first longitudinal profile and a first flow lumen;
   a second section having a second longitudinal profile and a second flow lumen; and
   a hinged connection free of the support components and between the first section and the second section;
   wherein the first flow lumen and the second flow lumen are opened during a deployment of the endoprosthesis and remain open during actuation of the hinged connection such that the first longitudinal profile is bent with respect to the second longitudinal profile.

2. The endoprosthesis of claim 1 wherein the hinged connection is actuated such that the first longitudinal profile is bent perpendicular with respect to the second longitudinal profile.

3. The endoprosthesis of claim 1 wherein the second section further comprises a third longitudinal profile and a third flow lumen.

4. The endoprosthesis of claim 3 wherein the second and third flow lumens have smaller diameters than the first flow lumen.

5. The endoprosthesis of claim 1 wherein the hinged connection isolates bending forces between the first and second sections.

6. The endoprosthesis of claim 5 wherein the first and second flow lumens exhibit diameter differential.

7. The endoprosthesis of claim 5 wherein the hinged connection forms at least one pleat when bent.

8. An endoprosthesis comprising:
   a single, continuous graft component combined with a plurality of support components, the combination comprising:
   a first section having a first longitudinal profile and a first flow lumen;
   a second section having a second longitudinal profile and a second flow lumen; and
   a hinged connection between the first section and the second section, the hinged connection isolating bending forces between the first and second sections;
   wherein the first flow lumen and the second flow lumen are opened during a deployment of the endoprosthesis and remain open during actuation of the hinged connection such that the first longitudinal profile is bent with respect to the second longitudinal profile, and wherein the first and second flow lumens exhibit diameter differential and adjacent ends of the first and second flow lumens telescope relative to one another.

9. The endoprosthesis of claim 8, wherein the hinged connection forms at least one pleat when bent.

10. The endoprosthesis of claim 8, wherein the hinged connection is actuated such that the first longitudinal profile is bent within 360 degrees with respect to the second longitudinal profile.

11. The endoprosthesis of claim 8, wherein adjacent ends of the first and second flow lumens have different diameters to allow one to move, at least partially, into the other at the hinged connection to allow for relative bending or twisting of the first and second sections.

12. A method for maintaining flow lumens of an endoprosthesis substantially open comprising:
    deploying an endoprosthesis at a treatment site, the treatment site comprising a turn and the endoprosthesis comprising:
    a single, continuous graft component having an uninterrupted outer surface combined with a plurality of support components, the combination comprising:
    a first section having a first longitudinal profile and a first flow lumen;
    a second section having a second longitudinal profile and a second flow lumen; and
    a hinged connection free of the support components and between the first section and the second section;
    wherein the first flow lumen and the second flow lumen are kept open when the hinged connection is actuated about the turn.

13. The method of claim 12 wherein the hinged connection is actuated such that the first longitudinal profile is bent within 360 degrees with respect to the second longitudinal profile.

14. The method of claim 12 wherein the endoprosthesis is a bifurcated stent graft and the second section further comprises a third longitudinal profile and a third flow lumen.

15. The method of claim 12 wherein the hinged connection does not transfer bending or twisting forces between the first and second sections.

16. The method of claim 15 wherein the hinged connection forms a plurality of pleats when bent.

17. The method of claim 15 wherein adjacent ends of the first and second flow lumens have different diameters to allow one to move, at least partially, into the other at the hinged connection to allow for relative bending or twisting of the first and second sections.

18. The method of claim 17 wherein one of the first and second flow lumens moves into the other more on the inside of the turn.

* * * * *